United States Patent
Annigeri et al.

(10) Patent No.: US 9,526,243 B2
(45) Date of Patent: Dec. 27, 2016

(54) POLLINATION SUCCESS AND SEED SET IN CORN HYBRID SEED PRODUCTION

(71) Applicants: Pioneer Hi-Bred International, Inc., Johnston, IA (US); E. I. DUPONT DE NEMOURS & COMPANY, Wilmington, DE (US)

(72) Inventors: Shivakumar G. Annigeri, Hyderabad (IN); Sarat P. Babu, Khammam (IN); Evandro Sidnei Georg, Itumbiara (BR); Jardel Lopes Pereira, Itumbiara (BR)

(73) Assignees: E I DU PONT DE NEMOURS AND COMPANY, Wilmington, DE (US); PIONEER HI BRED INTERNATIONAL INC, Johnston, IA (US)

( * ) Notice: Subject to any disclaimer, the term of this patent is extended or adjusted under 35 U.S.C. 154(b) by 0 days.

(21) Appl. No.: 14/419,845

(22) PCT Filed: Aug. 5, 2013

(86) PCT No.: PCT/US2013/053603
§ 371 (c)(1),
(2) Date: Feb. 5, 2015

(87) PCT Pub. No.: WO2014/025680
PCT Pub. Date: Feb. 13, 2014

(65) Prior Publication Data
US 2015/0201619 A1    Jul. 23, 2015

(30) Foreign Application Priority Data
Aug. 6, 2012    (IN) ............... 2451/DEL/2012

(51) Int. Cl.
*A01N 43/12*    (2006.01)
*A01H 3/04*    (2006.01)
*A01H 5/10*    (2006.01)

(52) U.S. Cl.
CPC ............ *A01N 43/12* (2013.01); *A01H 3/04* (2013.01); *A01H 5/10* (2013.01)

(58) Field of Classification Search
CPC ............ A01H 3/04; A01H 5/10; A01H 43/12
USPC ............................................. 504/297
See application file for complete search history.

(56) References Cited

U.S. PATENT DOCUMENTS

2011/0232247 A1*    9/2011    Zhu ..................... A01H 5/10
56/1

OTHER PUBLICATIONS

Chory et al.,Gibberellin-Induced changes in the populations of translatable mRNAs and accumulated polypeptides in dwarfs of maize and pea, Plant Physiology (1987) vol. 83 (1): 15-23.*
Naghashzadeh, et al.; "Evaluation of effects of gibberellic acid on maize (*Zea mays* L.) in different planting dates"; Plant Ecophysiology (2009) 3:159-162.*
Chory, et al.; "Gibberellin-Induced changes in the populations of translatable mRNAs and accumulated polypeptides in dwarfs of maize and pea", Plant Physiology (1987) vol. 83 (1): 15-23.
Cherry, et al.; "Effect of Gibberellic Acid on Growth and Yield of Corn", Agronomy J (1960) 52(3):167-170.
Espinosa et al.; "Options for Promoting the pollination and seed production of H-311 hybrid corn", Mesoamerican Agronomy (2001) 12(2):229-335.(Spanish version).
Espinosa et al.; "Options for Promoting the pollination and seed production of H-311 hybrid corn", Mesoamerican Agronomy (2001) 12(2):229-335.
Hartwig, et al.:"Brassinosteriod control of sex determination in maize", PNA, 2011 108(49):19814-19819.
Rood, et al.; "Changes of endogenous gibberellin-like substances with sex reversal of the apical inflorescence or corn", Plant Physiol, (1980) 66:793-796.
International Search Report and Written Opinion of the International Searching Authority for PCT/US2013/053603 mailed Nov. 13, 2013.

* cited by examiner

*Primary Examiner* — Janet Epps-Smith
*Assistant Examiner* — Courtney Brown
(74) *Attorney, Agent, or Firm* — Pioneer Hi-Bred Intl, Inc.

(57) ABSTRACT

The invention provides methods and process to enhance pollination success and thereby increase seed yield in corn seed production. The invention discloses use of Gibberellins to increase hybrid seed production in corn.

12 Claims, 7 Drawing Sheets

Number of secondary branches of the rachis

FIG. 5D

Pollen score

POLLINATION SUCCESS AND SEED SET IN CORN HYBRID SEED PRODUCTION

REFERENCE TO RELATED APPLICATIONS

This application is a US National Stage Entry under 35 U.S.C. §371 of International Patent Application No. PCT/US13/53603, filed on Aug. 5, 2013, which claims priority to Indian Provisional Patent Application No. 2451/DEL/2012, filed Aug. 6, 2012, the entire contents of each of which are herein incorporated by reference.

FIELD OF INVENTION

The present invention relates to methods and process to enhance pollination success and thereby increase seed yield in corn hybrid seed production.

BACKGROUND

Corn is an important and valuable field crop. Thus, a continuing goal of plant breeders is to develop high yielding maize hybrids that maximize the amount of grain produced with the inputs used and minimize susceptibility of the crop to environmental stresses. To accomplish that goal, the maize breeder must select and develop superior inbred parental lines for producing hybrids.

Commercial hybrid seed production, such as hybrid corn (maize, Zea mays) seed production, is an expensive and labor-intensive process. Hybrid corn seed production involves the production of male and female parent lines, and planting these in separate rows or blocks, in pollinating proximity, in an isolated field. The female parent plants must be treated to prevent pollen shed (e.g. manual or mechanical detasseling) to ensure only pollination by the male parent. Following pollination, the male parent plants must be destroyed, usually by a mechanical means, to prevent seed mixing during harvest. Ears from the cross-pollinated female parent are harvested, processed, and the hybrid seed sold to farmers for planting.

Hybrid seed yield depends in part on the efficiency of cross-pollination between the male and the female parent plants. Natural pollination occurs in maize when wind blows pollen from the tassels to the silks that protrude from the tops of the ears.

Increasing the efficiency of cross-pollination would increase the yield of the hybrid seeds in two ways: (1) Improved pollen dispersal can result in more seed produced per ear. (2) Improved pollen dispersal reduces the field area required for male parent plants and therefore increases the hybrid seed yield per unit area.

One means of increasing cross-pollination efficiency by increasing the dissemination of pollen is to use mechanical wind blowers. This wind blower is typically operated manually each day during the flowering time. Using wind blowers is tedious and time consuming, and benefits are unpredictable. The task needs to be repeated every day for 12 to 15 days, costing time and money.

It is desirable to find other means of increasing cross-pollination efficiency between the parent plants for hybrid maize production and hence increase hybrid seed yield.

SUMMARY

One embodiment of the present invention is a method of increasing corn hybrid seed production in a field comprising the steps of (a) growing male and female parent corn plants in a field; (b) treating the male parent plants with a Gibberellin; and (c) quantifying hybrid seed production; wherein hybrid seed production is increased with respect to a control planting, wherein the ratio of male plant height to female ear height at pollination is suboptimal in the control planting. In one embodiment, the step of treating the male parent plants with a Gibberellin is done by spraying the male parent plant with a Gibberellin.

In one embodiment, the male parent plants are treated with Gibberellin when they are in a vegetative stage V13 or above. In one embodiment, the male parent plants are treated with Gibberellin when they are in the V13-V17 stage. In another embodiment of the current invention the male parent plants are sprayed with a Gibberellin when a minimum of 80% of the male parent plants have the tassel wrapped in two leaves. In one embodiment of the invention, the Gibberellin is GA3. In one embodiment of the current invention, GA3 is sprayed at a dose of 10 g-60 g/1000 $m^2$ of field area planted to male parent plants. In one embodiment, GA3 is sprayed at a dose of 10 g/1000 $m^2$ of field area planted to male parent plants. In one embodiment of the current invention, GA3 is sprayed at a dose of 4 g-60 g/1000 $m^2$ of field area planted to male parent plants.

In one embodiment of the invention, GA3 is applied in a formulation having 90% active ingredient.

In one embodiment, the male parent is an inbred and the female parent is a hybrid. In one embodiment, the ratio of male parent plant height to female parent ear height at pollination in the control planting is equal to or less than about 2.0. In one embodiment, the ratio of field area planted to male parent plants to the field area planted to female parent plants is reduced with respect to the control planting.

In another embodiment, hybrid maize seed production is increased by at least 5% by using the methods disclosed herein. In another embodiment of the current invention, hybrid maize seed production is increased by at least 30% by using the methods disclosed herein. In another embodiment, the hybrid seed production is increased by at least 40%.

BRIEF DESCRIPTION OF DRAWINGS

The invention can be more fully understood from the following detailed description and the accompanying drawings

FIG. 4 shows the effect of 1 or 2 GA3 treatments on plants in primary and secondary plantings of Inbred B, when compared to a control treatment.

FIG. 5 shows the effect of 1 or 2 GA3 treatments on plants of Inbred C when compared to a control treatment.

DETAILED DESCRIPTION OF THE INVENTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

As used herein:

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

"Progeny" comprises any subsequent generation of a plant.

"Phenotype" means the detectable characteristics of a cell or organism.

The term "crossed" or "cross" means the fusion of gametes via pollination to produce progeny (e.g., cells, seeds or plants). The term encompasses both cross pollination and self pollination ("selfing"). The term "crossing" refers to the act of fusing gametes via pollination to produce progeny.

The development of hybrid maize involves three major steps: (1) the selection of plants from various germplasm pools; (2) the selfing of the selected plants for several generations to produce a series of inbred lines, which, although different from each other, breed true and are highly uniform; and (3) the crossing of selected inbred lines with unrelated inbred lines to produce the hybrid progeny (F1), which are evaluated.

An important consequence of the homozygosity and homogeneity of the inbred lines is that the hybrid between any two inbreds will always be the same. Once the inbreds that give a superior hybrid have been identified, the hybrid seed can be reproduced indefinitely as long as the homogeneity of the inbred lines is maintained.

Plants that have been self-pollinated and selected for type for many generations become homozygous at almost all gene loci and produce a uniform population of true breeding progeny. A cross between two homozygous lines produces a uniform population of hybrid plants that may be heterozygous at a number of gene loci. A cross of two plants each heterozygous at a number of gene loci will produce a population of hybrid plants that differ genetically and will not be uniform.

Maize is bred through techniques that take advantage of the plant's method of pollination (Espinosa, A. et al. (2001) *Agronomia Mesoamericana* 12(2): 229-235; Cherry, J. et al (1960) *Agronomy Journal*, 52 (3): 167-170).

A plant is self-pollinated if pollen from one flower is transferred to the same or another flower of the same plant or a genetically identical (isogenic) plant. A plant is cross-pollinated if the pollen comes from a flower on a genetically different plant.

Maize can be bred by both self-pollination and cross-pollination techniques. Maize has separate male and female flowers on the same plant, located on the tassel and the ear, respectively. Natural pollination occurs in maize when pollen falls or is blown from the tassels to the silks that protrude from the tops of the ears.

An "inbred maize" line is a homozygous true breeding strain of corn maintained by self- or sib-pollination.

As used herein the term "internode" is defined as the part of the plant stem between the two successive nodes.

As used herein the term "node" is defined as the part of the plant stem where one or more leaves arise. It is one leaf in the case of maize.

As used herein the term "ear node" is defined as a node at which an ear develops; or where the ear shank attaches to the stalk.

"Plant height" is a measure of the height of the plant from the soil surface to the tip of the tassel.

"Ear Height" is measured from the soil surface to the point where the ear shank attaches to the stalk (Ear Node).

"Vegetative (V) stages" or "Vegetative (V) leaf stages" are determined by the total number of leaves with visible collars (e.g., a plant with three visible leaf collars is at V3). A collar is the off-white band at the base of the leaf blade where it extends away from the stalk.

V13-V17 leaf stages are the vegetative leaf 13 to vegetative leaf 17 stages of corn. At some point between the V13-V17 leaf stages, the tip of the tassel becomes visible.

Vn vegetative stage would indicate "n" leaf collars present; there are 17-22 vegetative stages before tassel emergence is complete.

Vegetative and reproductive stages are determined on a whole-field basis when at least 50 percent of the plants have reached or are beyond a particular stage (Corn field guide; Iowa State University; ed. by Daren Mueller and Rich Pope; Brent Bean and Carl Patrick; *Corn Development and Key Growth Stages*).

F1 Hybrid is the first generation progeny of the cross of two non-isogenic plants.

A single cross hybrid is produced when two inbred lines are crossed to produce the F1 progeny ($1^{st}$ generation).

A multiple-cross hybrid is the first generation of a cross involving more than four inbred lines, i.e., a cross of two double crosses, a single-cross hybrid crossed with a double-cross hybrid, etc.

A three-way hybrid is the first generation of a cross between a single-cross hybrid and an inbred ((A×B)×C).

A double cross hybrid is produced from four inbred lines crossed in pairs (A×B and C×D) and then the two F1 hybrids are crossed again ((A×B)×(C×D)).

Backcrossing can be used to improve an inbred line. Backcrossing transfers a specific desirable trait from one inbred or source to an inbred lacking that trait. This can be accomplished for example by first crossing a superior inbred (A) (recurrent parent) to a donor inbred (non-recurrent parent), which carries the appropriate gene(s) for the trait in question. The progeny of this cross is then mated back to the superior recurrent parent (A) followed by selection in the resultant progeny for that desired trait to be transferred from the non-recurrent parent. After five or more backcross generations with selection for the desired trait, the progeny will be heterozygous for loci controlling the trait being transferred, but will be like the superior parent for most or almost all other genes. The last backcross generation would be selfed to give pure breeding progeny of the gene(s) being transferred.

For efficient cross pollination between the male parent plant and the female parent plant to occur, the ratio of the male parent plant height to the ear height on the female parent plant is important. A ratio of male parent plant height to female parent ear height that would result in suboptimal cross-pollination efficiency is referred to herein as "suboptimal ratio". The "suboptimal ratio of male parent plant height to female parent ear height" as referred to herein is a ratio approximately at or below 2.0. A ratio in the range of 2.1-5.5 is considered optimal.

Gibberellins are a class of diterpenoid plant hormones (see, e.g., Krishnamoorthy (1975) Gibberellins and Plant Growth, John Wiley & Sons). Examples of gibberellins useful in the practice of the present methods include, but are not limited to, gibberellin A1 (GA1), gibberellin A3 (GA3), gibberellin A4 (GA4), gibberellin A7 (GA7), or a combination of two or more thereof. For example, GA4/7 (also referred to as Gibberellin 4/7) indicates a mixture of GA4 and GA7.

The term "treatment" or "treating" herein refers to subjecting the male parent plants to a Gibberellin. Examples of ways in which the male parent plants can be treated include, but are not limited to, spraying, drenching, swab application, injecting, dusting, and slurry application. A control planting is defined herein as a planting for producing hybrid maize seeds, where there is no Gibberellin application on the male parent plants.

As used herein the term "active ingredient" refers to the biologically active component of the commercially available Gibberellin formulation.

Embodiments

One embodiment of the present invention is a method of increasing corn hybrid seed production in a field comprising the steps of (a) growing male and female parent corn plants in a field; (b) treating the male parent plants with a Gibberellin; and (c) quantifying hybrid seed production; wherein hybrid seed production is increased with respect to a control planting, wherein the ratio of male parent plant height to female parent ear height at pollination is suboptimal in the control planting. In one embodiment, the step of treating the male parent plants with a Gibberellin is done by spraying the male parent plant with a Gibberellin.

In one embodiment, the male parent plants are treated with Gibberellin when they are in a vegetative stage V13 or above. In one embodiment, the male parent plants are treated with Gibberellin when they are in the V13-V17 stage. In another embodiment of the current invention the male parent plants are sprayed with a Gibberellin when a minimum of 80% of the male parent plants have the tassel wrapped in two leaves. In one embodiment of the invention, the Gibberellin is GA3. In one embodiment of the current invention, GA3 is sprayed at a dose of 10 g-60 g/1000 m$^2$ of field area planted to male parent plants. In one embodiment, GA3 is sprayed at a dose of 10 g/1000 m$^2$ of field area planted to male parent plants.

In one embodiment, GA3 is applied at a dose of 4 g-60 g/1000 m$^2$ of field area planted to male parent plants.

In one embodiment, the effective concentration of the GA3 depends on the % of active ingredient in the commercially available GA3 formulation. In one embodiment of the invention, the effective concentration of the GA3 applied can be calculated based on the "% active ingredient" of the commercially available GA3 formulation. In one embodiment of the invention, the GA3 applied has 90% active ingredient. In one embodiment of the current invention, the male parent is an inbred and the female parent is a hybrid. In one embodiment, the ratio of male parent plant height to female parent ear height at pollination in the control planting is equal to or less than 2.0. In one embodiment, the ratio of field area planted to male parent plants to the field area planted to female parent plants is reduced with respect to the control planting.

In certain embodiments of the current invention, hybrid maize seed production, as measured by volume or by mass or by seed count, for example, is increased by at least 5% by using the methods disclosed herein. In another embodiment of the current invention, hybrid maize seed production is increased by at least 30% by using the methods disclosed herein. In certain embodiments, the hybrid seed production is increased by at least 40%. In certain embodiments the method enhances hybrid seed yield, relative to the hybrid seed yield in a control planting. In an embodiment, hybrid seed yield is enhanced by at least 5%, 6%, 7%, 8%, 9%, 10%, 11%, 12%, 13%, 14%, 15%, 16%, 17%, 18%, 19%, 20%, 25%, 30%, 35%, 40% or 45%.

In one embodiment, when GA3 is sprayed on male parent plant at a given dosage, the last few internodes are elongated and the plant height is increased. In one embodiment, the male parent plant height is increased by at least 20 centimeters (cm). In one embodiment, the male parent plant height is increased by at least 30 cm.

In one embodiment, the ratio of male parent plant height to female parent ear height is increased from 2.02 in control (no GA3 spray) to 2.40 after spray.

In certain embodiments, the desired result of increasing the plant height is achieved without any negative or deleterious effects on other plant processes.

In certain embodiments, the method reduces the cost of hybrid seed production.

As will be evident to a person of ordinary skill in the art, the method of increasing hybrid seed yield disclosed herein can be used in any seed production system where the ratio of male parent plant height to female parent ear height is suboptimal. The method of increasing hybrid seed yield disclosed herein can be used in many seed production systems where the parent crosses for hybrid seed production include, but are not limited to any of the following: A single cross, a modified single cross (such as, a first generation cross between two inbred lines, one or other of which may have been modified slightly by the use of closely related crossing), a double cross, a three-way cross, a top cross (such as, the first generation of a cross between an open-pollinated variety, and inbred line or a single-cross).

The dosage of 10-60 g GA3/1000 m$^2$ of field area planted to male parent plants can be used in seed production systems where female parent and male parent plants are planted in pollinating proximity.

The female parent and male parent plants are planted in a field in pollinating proximity at a ratio that saves field space or provides optimal hybrid seed production.

As will be evident to one of ordinary skill in the art, the female parent and male parent plants can be planted in different row ratios; examples include but are not limited to, a ratio of from 1 female parent plant row to 1 male parent plant row, 2 female parent plant rows to 1 male parent plant row, 3 female parent plant rows to 1 male parent plant row, 4 female parent plant rows to 1 male parent plant row, 5 female parent plant rows to 1 male parent plant row, 6 female parent plant rows to 1 male parent plant row, 7 female parent plant rows to 1 male parent plant row, 8 female parent plant rows to 1 male parent plant row, 9 female parent plant rows to 1 male parent plant row or 10 or more female parent plant rows to 1 male parent plant row, to optimize the field space or hybrid seed production.

EXAMPLES

The present invention is further illustrated in the following Examples, in which parts and percentages are by weight and degrees are Celsius, unless otherwise stated. It should be understood that these examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Furthermore, various modifications of the invention in addition to those shown and described herein will be apparent to those skilled in the art from the foregoing description. Such modifications are also intended to fall within the scope of the appended claims.

Example 1

Hybrid A is a three-way corn hybrid which performs well in rain-fed areas in India. The female parent of this hybrid is a single cross and male parent is an inbred. The male is significantly shorter and weaker than the female. The ear height in female is 94 cm and male plant height (including tassel length) is 190 cm. The ratio of male parent plant height to female parent ear height is 2.02. This is not favorable for pollen dispersal and cross fertilization. A taller male gives a very clear advantage in easy spread of pollen. Further, a height disadvantage is amplified where the female is a single cross and male is inbred, as the robust female parent suppresses male parent growth. Adequate pollen from male does not reach the silks in female, rendering poor seed set. With less seed yield due to low seed set, seed production may be uneconomical in Hybrid A. Controlled use of Gibberellic Acid as foliar spray for male parent helped increase the plant height and thereby facilitated easier dispersal of pollen for better pollination success.

When GA3 was sprayed on male parent at a given dosage, the last few internodes were elongated and the plant height was increased by 33 cm. The ratio of male parent plant height to female parent ear height increased from 2.02 in control (no GA3 spray) to 2.40 after spray. This spray was done when a minimum of 80% of the plants had the tassel wrapped in two leaves. The desired result of increasing the plant height was achieved without any negative or deleterious effects on other plant processes.

A field trial was conducted to study the impact of GA3 on male parent plant height and also seed yield in hybrid seed production. GA3 dose of 10 g (dissolved in 100 ml alcohol) was sprayed in one acre of male plants (25% of area in 3:1 row ratio) when male tassel is wrapped up in two leaves.

Figure 1:
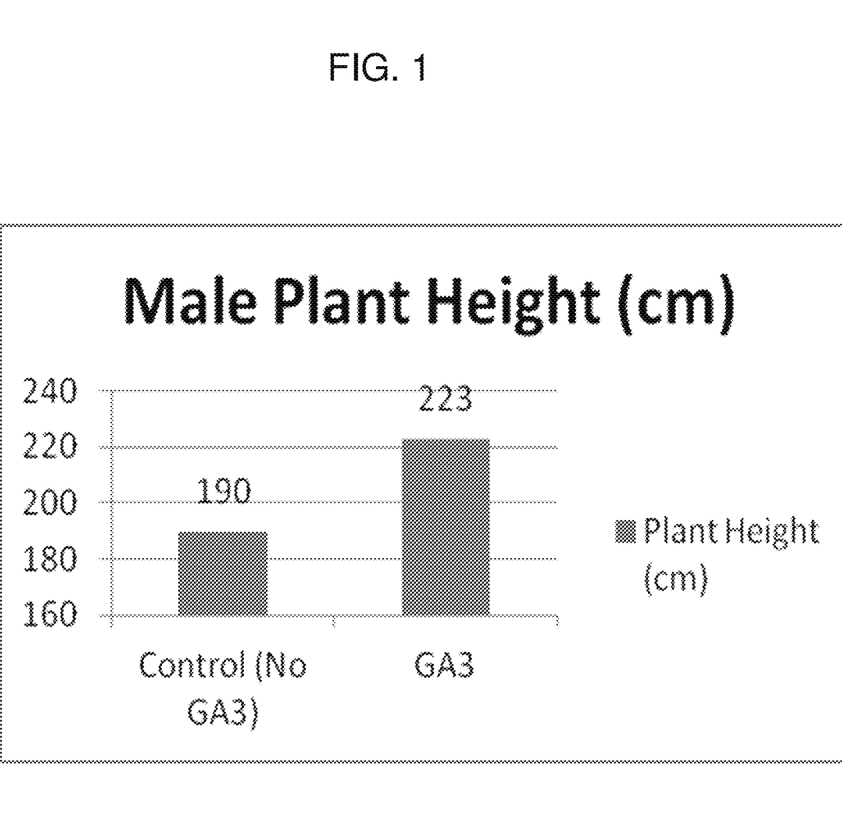
FIG. 1 shows the increase in plant height of the male parent plant of Hybrid A after spraying GA3.

As shown in FIG. 1, the male parent plant height increased 17%, from 190 cm to 223 cm, after spraying GA3. In seed production taller males are preferred as it helps in better pollen dispersal and allows more female plant area.

Figure 2:
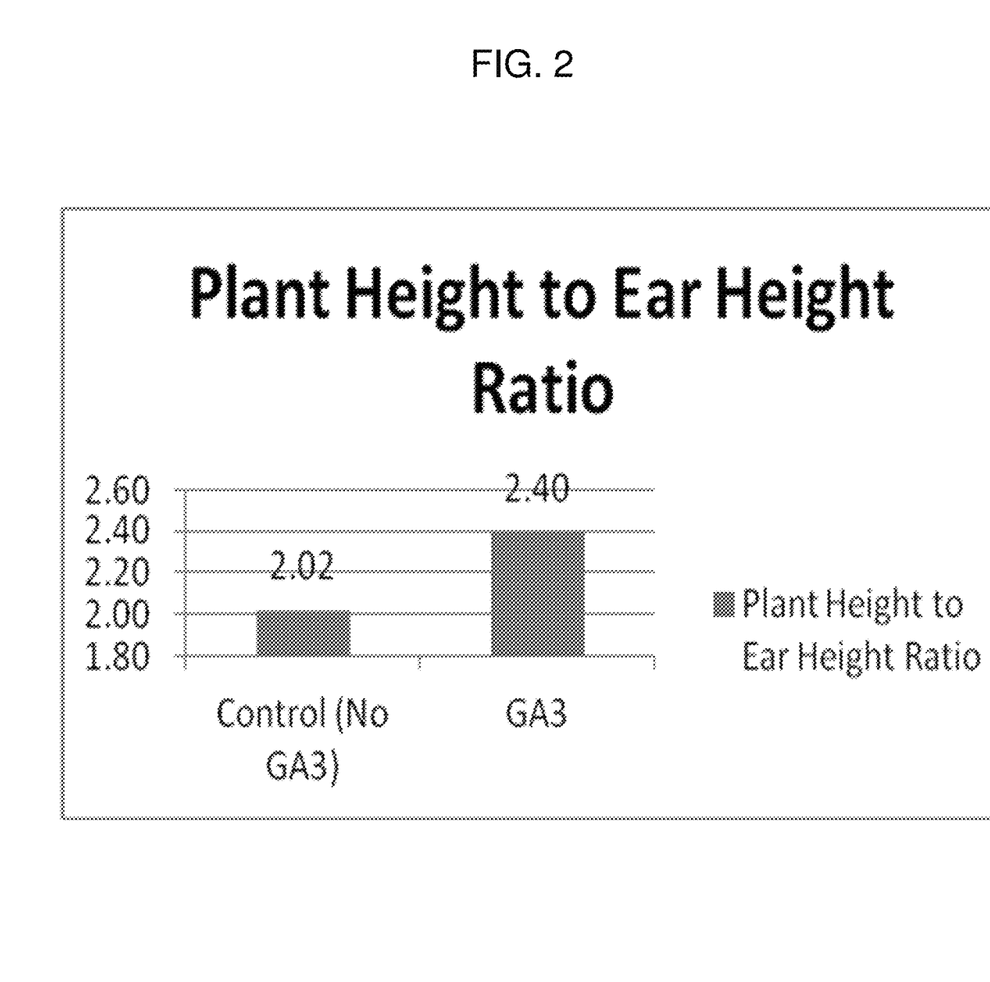
FIG. 2 shows the increase in the ratio of Hybrid A male parent plant height to female parent ear height after spraying GA3.

With the increase in male plant height there was an increased ratio of male parent plant height to female plant ear height. As shown in FIG. 2, the ratio increased from 2.02 to 2.40. In seed production higher ratio is usually preferred and advantageous.

Figure 3:
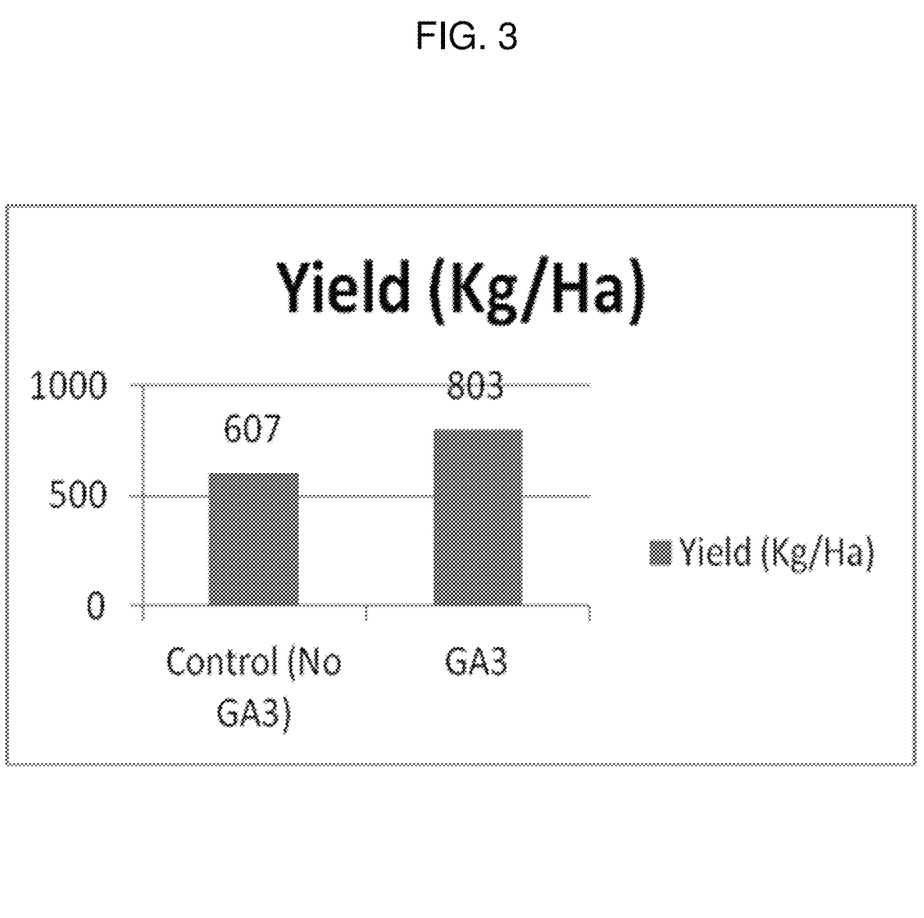
FIG. 3 shows the yield increase of hybrid seed after GA3 treatment of the male parent plants.

This increase in male height also contributed positively on the seed yield (FIG. 3). In the experimental plot the yield increased from 607 Kg/Acre to 803 Kg/Acre, a significant yield improvement of 32% noticed with the GA3 treatment.

The method achieves significantly higher pollination success and so higher seed yields. The methodology is easy to follow and monitor at field level. The results are predictable. Therefore, seed production becomes not only reliable but also economical. With minimum calibration, this methodology can be adopted in other corn hybrids which have a shorter male parent.

Example 2

GA3 spray to increase male inbred height was also tested with 2 more inbreds, Inbred B and Inbred C, in Brazil.

Inbred B was sown in two sequential plantings, separated by 80 to 100 heat units. The first planting is referred to as the primary male; the second planting is referred to as the secondary male. The two male plantings were separated in the field by 40 cm; minimum distance from female rows was 70 cm.

Data were collected after the following treatments: (a) control, (b) GA3: one application, before flowering, when the tassel is enveloped in 2 leaves; (b) GA3: 2 sequential applications, one at V6 stage and 1 application before flowering. The concentration of GA3 used was 365 g of GA3 (10% active ingredient) per hectare (which is approximately equivalent to 40 g of GA3 at 90% active ingredient), and the spray volume was 130 liters/hectare.

The plot had 5.20 meter length of each row and 60 cm between plots. Ten male plants in sequence for each male row (primary male and secondary male separate) were measured and the average calculation was obtained and replicated 5 times in different plots. Measurements taken were plant height; length of primary rachis of the tassel; number of secondary tassel branches; and visual pollen score where 1=no pollen (sterile), 5=average amount of pollen, and 9=large amount of pollen.

Figure 4A:
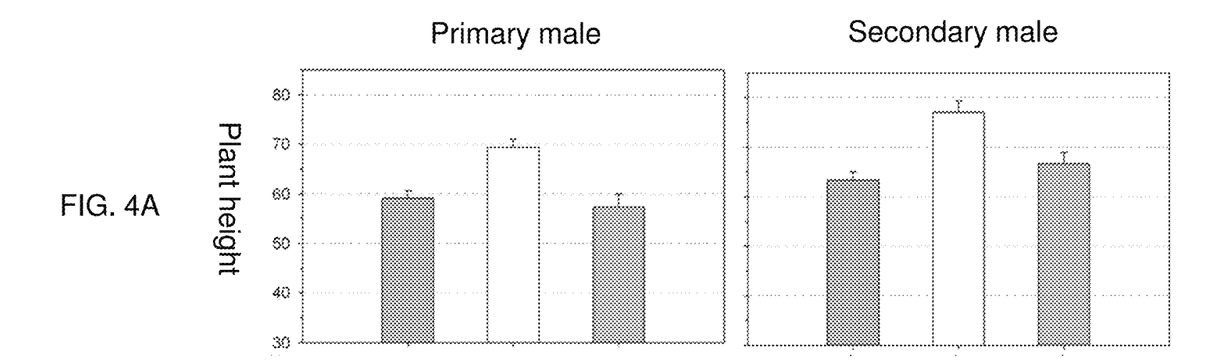
FIG. 4A and FIG. 4B show the effect of GA3 treatment on plant height and length of primary tassel rachis, respectively, in centimeters (cm).
Figure 4B:
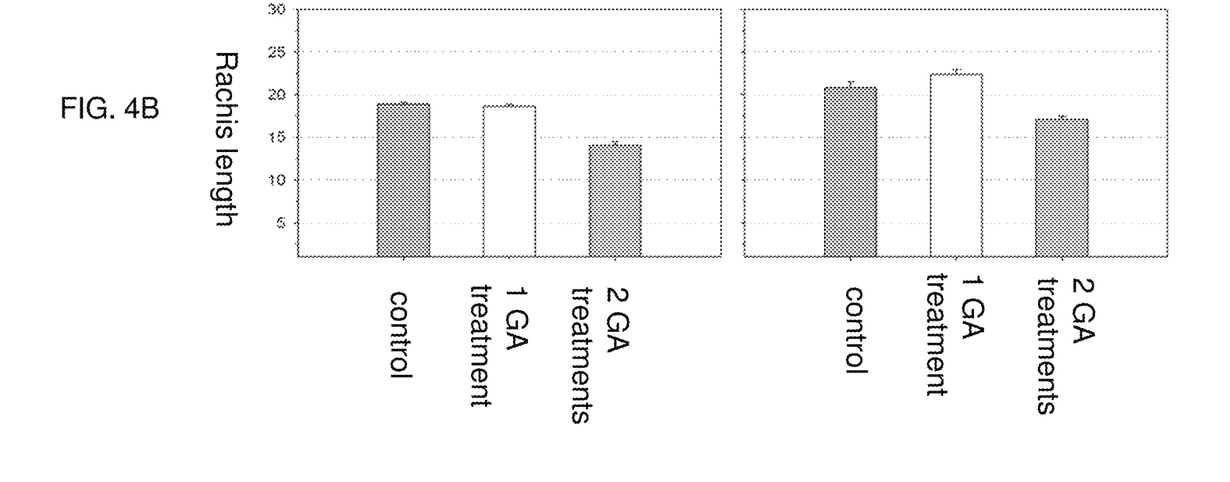
Figure 4C:
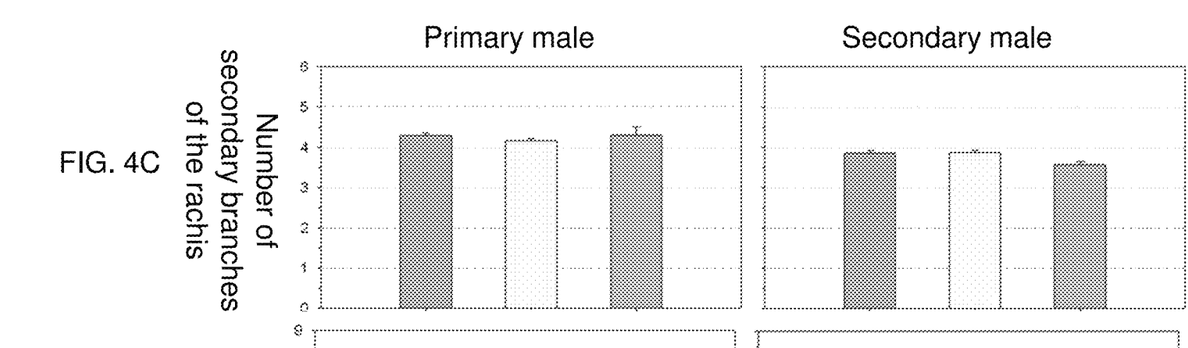
FIG. 4C and FIG. 4D show the effect of GA3 treatment on number of secondary branches from rachis and pollen score, respectively.
Figure 4D:
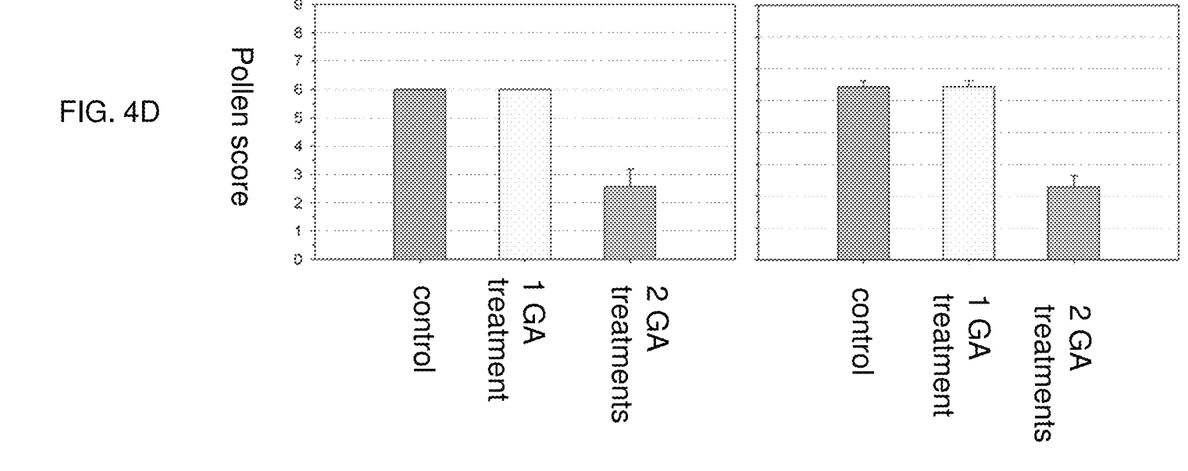

The results for Inbred B are shown in FIG. 4A-4D. As can be seen in FIG. 4A, plant height increased by about 10 cm in the primary males, and by almost 15 cm in secondary males after one application of GA3. Primary rachis length, number of secondary branches on the rachis, and pollen score did not change significantly with one GA application, as seen in FIG. 4B-4D.

However, when two sequential GA treatments were applied to Inbred B, the size of the main rachis and the pollen score were reduced, relative to the control, in both primary and secondary males. The height of inbred B male parent plants was also seen to increase further by increasing the concentration of GA3 to 16 g/1000 $m^2$ of male plants.

Figure 5A:
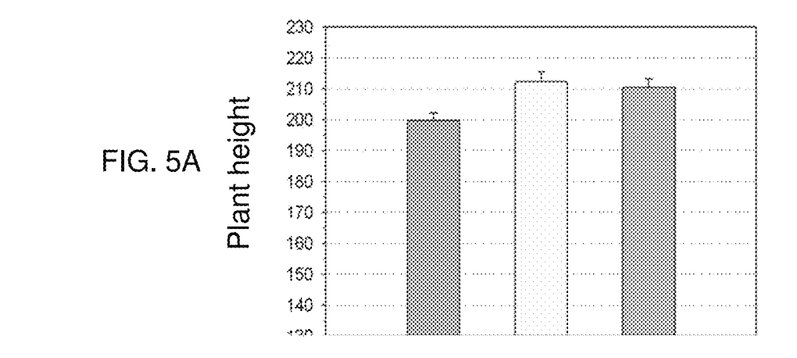
FIG. 5A and FIG. 5B show the effect of GA3 treatment on plant height and length of primary rachis, respectively, in centimeters (cm).
Figure 5B:
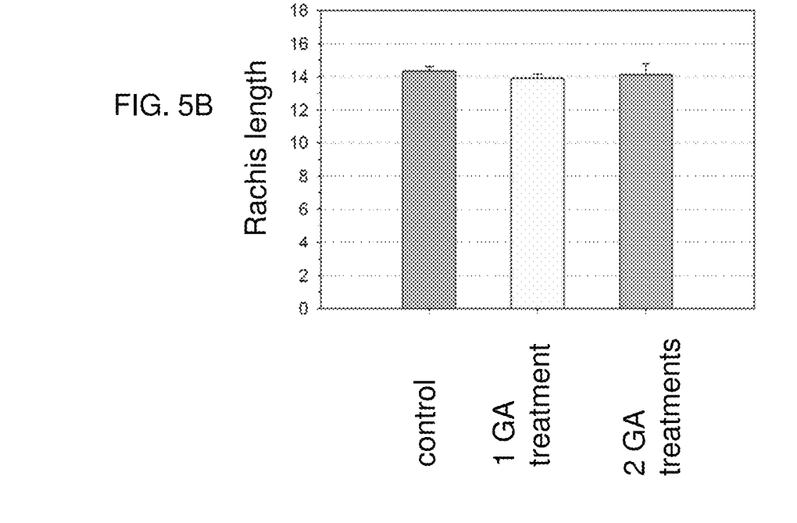
Figure 5C:
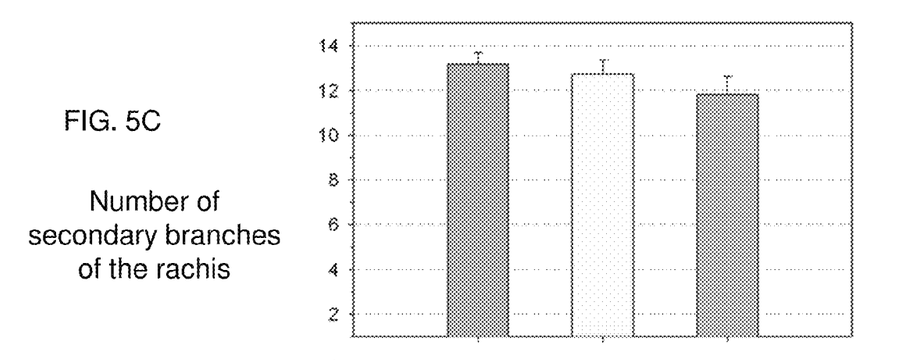
FIG. 5C and FIG. 5D show the effect of GA3 treatment on number of secondary branches from rachis and pollen score, respectively.
Figure 5D:
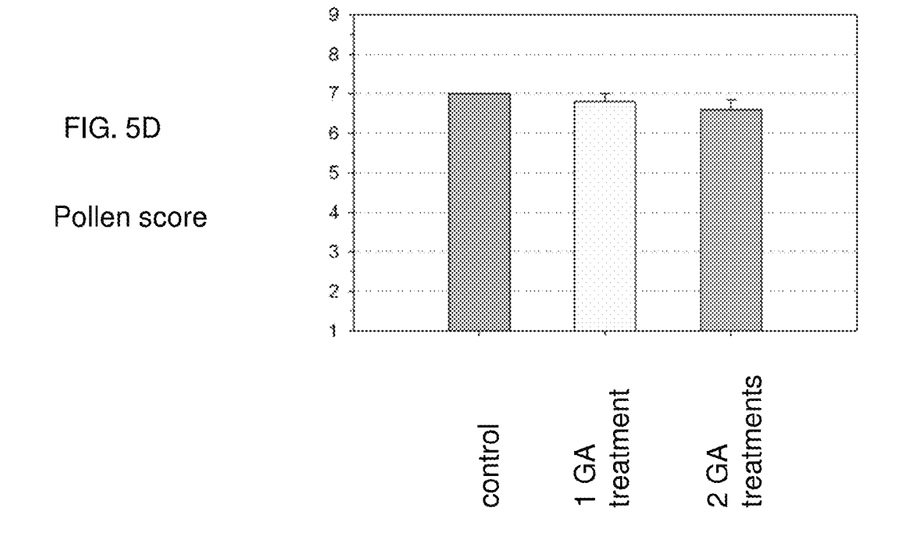

The results for Inbred C are shown in FIG. 5A-5D. As can be seen, plant height increased by almost 12 cm after one application of GA3. Primary rachis length, number of secondary branches on the rachis, and pollen score did not change significantly by one GA application, as seen in FIG. 5B-5D. A second application of GA was not more favorable than a single application.

In summary, the single gibberellic acid application at the pre-flowering stage promoted the growth of both male inbreds, and did not affect the parameters of main rachis size, number of primary and secondary branches and visual pollen score.

We claim:

1. A method of increasing corn hybrid seed production in a field comprising the steps of:
    (a) growing male and female parent corn plants in pollinating proximity;
    (b) treating the male parent plants with a Gibberellin when a minimum of 80% of the male parent plants have the tassel wrapped in two leaves, wherein the male parent plants are in the V13-V17 stage; and
    (c) quantifying hybrid seed production wherein hybrid seed production is increased with respect to a control planting and further wherein the ratio of male parent plant height to female parent ear height at pollination is suboptimal in the control planting.

2. The method of claim 1 wherein the step b) of treating the male parent plants with a Gibberellin is done by spraying the male parent plants with a Gibberellin.

3. The method of claim 2, wherein the Gibberellin is GA3.

4. The method of claim 1, wherein the male parent is an inbred and the female parent is a hybrid.

5. The method of claim 3 wherein the GA3 is sprayed at a dose of 10 g-60 g/1000 m$^2$ of field area planted to male parent plants.

6. The method of claim 3 wherein the GA3 is sprayed at a dose of 10 g/1000 m$^2$ of field area planted to male parent plants.

7. The method of claim 3 wherein the GA3 is sprayed at a dose of 4 g-60 g/1000 m$^2$ of field area planted to male parent plants.

8. The method of claim 1, wherein the hybrid seed production is increased by at least 5%.

9. The method of claim 1, wherein the hybrid seed production is increased by at least 30%.

10. The method of claim 1, wherein the hybrid seed production is increased by at least 40%.

11. The method of claim 1, wherein the ratio of male parent plant height to female parent plant ear height at pollination in the control planting is equal to or less than 2.0.

12. The method of claim 1, wherein the ratio of field area planted to male parent plants to the field area planted to female parent plants is reduced with respect to the control planting.

* * * * *